US007060876B2

(12) United States Patent
Hiei et al.

(10) Patent No.: US 7,060,876 B2
(45) Date of Patent: *Jun. 13, 2006

(54) METHOD FOR TRANSFORMING MONOCOTYLEDONS

(75) Inventors: Yukoh Hiei, Iwata-gun (JP); Toshihiko Komari, Iwata-gun (JP)

(73) Assignee: Japan Tobacco Inc., Tokyo (JP)

( * ) Notice: Subject to any disclaimer, the term of this patent is extended or adjusted under 35 U.S.C. 154(b) by 52 days.

This patent is subject to a terminal disclaimer.

(21) Appl. No.: 09/229,324

(22) Filed: Jan. 13, 1999

(65) Prior Publication Data

US 2002/0178463 A1 Nov. 28, 2002

Related U.S. Application Data

(63) Continuation of application No. 08/668,464, filed on Jun. 25, 1996, now abandoned, which is a continuation-in-part of application No. 08/193,058, filed as application No. PCT/JP93/00925 on Jun. 7, 1993, now Pat. No. 5,591,616.

(30) Foreign Application Priority Data

Jul. 7, 1992 (JP) ................................. 04/204464

(51) Int. Cl.
*A01H 1/00* (2006.01)
*A01H 5/00* (2006.01)
*C07H 2/04* (2006.01)
*C12N 15/82* (2006.01)
*C12N 15/84* (2006.01)

(52) U.S. Cl. ...................... 800/294; 800/278; 800/320; 800/320.2; 435/320.1; 435/419; 435/430; 435/430.1; 435/469; 536/23.1

(58) Field of Classification Search ............. 800/320.1, 800/278, 294, 320.2, 300.01, 320; 435/430, 435/430.1, 320.1, 469, 419; 536/23.1; 439/419
See application file for complete search history.

(56) References Cited

U.S. PATENT DOCUMENTS

| 4,940,838 | A | 7/1990 | Schilperoort et al. |
| 5,149,645 | A | 9/1992 | Hoekema et al. |
| 5,164,310 | A | 11/1992 | Smith et al. |
| 5,177,010 | A | 1/1993 | Goldman et al. |
| 5,187,073 | A | 2/1993 | Goldman et al. |
| 5,460,952 | A | 10/1995 | Yu et al. |
| 5,591,616 | A * | 1/1997 | Hiei et al. ............... 435/172.3 |
| 5,712,112 | A | 1/1998 | Yu et al. |
| 6,215,051 | B1 | 4/2001 | Yu et al. |

FOREIGN PATENT DOCUMENTS

| EP | 116718 | 8/1984 |
| EP | 120516 | 10/1984 |
| EP | 159418 | 10/1985 |
| EP | 176112 | 4/1986 |
| EP | 290799 | 11/1988 |
| EP | 320500 | 6/1989 |
| EP | 05 04869 A2 | 9/1992 |
| EP | 05 86355 A2 | 3/1994 |
| EP | 06 04662 A1 | 7/1994 |
| EP | 06 72752 A1 | 9/1995 |
| JP | 90411681 | 12/1990 |
| JP | 7143895 A | 6/1995 |
| WO | WO8603776 | 7/1986 |
| WO | WO 8912102 | 12/1989 |
| WO | 92 09696 | 6/1992 |

OTHER PUBLICATIONS

Gould et al, Plant Physiol. Transformation of *Zea mays* L. using Agrobacterium tumefaciens and the shoot apex. (1991) 95, 426-434.*
Graves et al, The transformation of *Zea mays* seedlings with Agrobacterium tumefaciens. Plant Molecular Biology (1986) 7, 43-50.*
Rieger, et. al., Glossary of Genetics and Cytogenetics, 1976, Springer-Verlag, New York, see p. 139.*
Dale et. al., Agroinfection of Wheat: inoculation of in vitro grown seedlings and embryos, Plant Science, 1989, vol. 63, pp. 237-245.*
Fraley, et. al., Proc. Natl. Acad. Sci. USA, vol. 80, 1983, pp. 4803-4807.*
Grimsley, et. al. Biotechnology, vol. 6, 1988, pp. 185-189.*
Green et al (1975, Crop Science 15: 417-421, cited by Applicants).*
Green (1982, Proc. Fifth International Congress of Plant Tissue and Cell Culture, pp. 107-108, cited by Applicants).*
Vasil et al (1987, Theoretical and Applied Genetics 73: 793-798).*

(Continued)

*Primary Examiner*—David T. Fox
*Assistant Examiner*—Georgia Helmer
(74) *Attorney, Agent, or Firm*—Birch, Stewart, Kolasch & Birch, LLP (57) ABSTRACT

The invention relates to a method for transforming a monocotyledonous plant. The time required from transformation to regeneration of a plant is shorter using the inventive method so that the frequency of emergence of mutants is smaller than the conventional methods. The inventive method may be generally applied even to the plants for which a regeneration method from a protoplast to a plant has not been established, and with which the preparation of the material to be subjected to the method is easy. That is, the present invention provides a method for transforming a monocotyledonous plant, comprising contacting a cultured tissue of said monocotyledonous plant during dedifferentiation thereof obtained by culturing an explant on a dedifferentiation-inducing medium for less than 7 days with a bacterium belonging to the genus *Agrobacterium* containing a super binary vector having the virulence region of a Ti plasmid, left and right border sequences of T-DNA of a Ti plasmid or an Ri plasmid of a bacterium belonging to the genus *Agrobacterium*, and a desired gene located between said left and right border sequences.

20 Claims, 2 Drawing Sheets

OTHER PUBLICATIONS

Rhodes et al (1988, BioTechnology 6: 56-60, cited by Applicants).*
Potrykus (1990, BioTechnology 8: 535-542, cited by Applicants).*
Lupotto et al. (1988) *Maydica* 33:163-177.
Mikami et al. (1988) *Plant Cell, Tissue and Organ Culture* 12:311-314.
Saito et al. (1992) *Theoretical and Applied Genetics* 83:679-683.
Komari et al. (1989) *Theoretical and Applied Genetics* 77:547-552.
Komari (1989) *Plant Science* (1989) 60:223-229.
Drlica et al. (1974) *Proc. Natl. Acad. Sci USA* 71:3677-3681.
Pietrzak et al. (1986) *Nucleic Acids Research* 14:5857-5868.
Ohta et al. (1990) *Plant Cell Physiol.* 31(6) :805-813.
Murashige et al. (1962) *Physiologia Plantarum* 15:473-497.
Toriyama et al. (1985) *Plant Science* 41:179-183.
Ditta et al. (1980) *Proc. Natl. Acad. Sci. USA* 77:7347-7351.
Horsch et al. (1984) *Science* 223:496-499.
Herrera-Estrella et al. (1983) *The EMBO Journal* 2(6) :987-995.
Jin et al. (1987) *Journal of Bacteriology* 169(10) :4417-4425.
Komari et al. (1986) *Journal of Bacteriology* 166(1) :88-94.
Linsmaier et al. (1965) *Physiologia Plantarium* 18:100-127.
Hood et al. (1984) *Biotechnology* 2:702-709.
Hood et al. (1986) *Journal of Bacteriology* 168(3) :1283-1290.
Toriyama et al. (1988) *Bio/Technology* 6 :1072-1074.
Shimamoto et al. (1989) *Nature* 338:274-277.
Rhodes et al. (1988) *Science* 240:204-207.
Zhang et al. (1988) *Theoretical and Applied Genetics* 76:835-840.
Datta et al. (1990) *Bio/Technology* 8:736-740.
Gordon-Kamm et al. (1990) *The Plant Cell* 2:603-618.
Christou et al. (1991) *Bio/Technology* 9:957-962.
Fromm et al. (1990) *Bio/Technology* 8:833-839.
Töpfer et al. (1989) *The Plant Cell* 1:133-139.
Caboche et al. (1990) *Physiol. Plant.* 79:173-176.
Gad et al. (1990) *Physiologia Plantarum* 79:177-183.
Neuhaus et al. (1987) *Theoretical and Applied Genetics* 75:30-36.
*The Botanical Review* 390-466.
Bytebier et al. (1987) *Proc. Natl. Acad. Sci. USA* 84:5345-5549.
Schäfer et al. (1987) *NATURE* 327:529-533.
Potrykus (Jun., 1990) *Bio/Technology*, 535-542.
Grimsley et al. (1987) *NATURE* 325(8) :177-179.
Grimsley et al. (1988) *Bio/Technology* 6:185-189.
Grimsley et al. (1989) *Mol Gen Genet* 217:309-316.
Gould et al. (1991) *Plant Physiol.* 95:426-434.
Mooney et al. (1991) *Plant Cell, Tissue and Organ Culture* 25:209-218.
Raineri et al. (1990) *Bio/Technology* 8:33-38.
Chih-ching (1981) *Plant Tissue Culture*, Pitman, Boston, pp. 43-50.
Gritz et al. (1983) *Gene* 25:179-188.
De Greve et al. (1981) *PLASMID* 6:235-248.
Luo et al. (1988) *Plant Molecular Biology Reporter* 6(3) :165-174.
Li et al. (1991) Science in China (Series B), vol. 34(8), pp. 923-931.
Chan et al. (1992) Plant Cell Physiol. 33(5) pp. 577-583.
Li et al. (1991) Science in China (Series B), vol. 34 (1), pp. 54-63.
Yao et al. (1990) Chinese J. Bot 2(2) :81-87.
Lee et al. (1991) Proc.Nat'l.Acad.Sci. USA 88(15)6389-93.
Sangwan et al. (1991) Mol. and Gen. Genetics, vol. 230, pp. 475-485.
Chem.Abstracts (1988) vol. 109(13), Abstract No. 105884.
Ingo Potrykus (1990) Biotechnology vol. 8, pp. 535-542.
Schlappi et al. (1992) The Plant Cell vol. 4, pp. 7-16.
Gould et al. (1991) Plant Physiology vol. 95, pp. 426-434.
Ishida et al. (1996), Nature Biotechnology, V.14, pp. 745-750.
Chan et al. (1993) Plant Molecular Biology 22:491-506.
Hiei et al. (1994) The Plant Journal 6(2), 271-282.
Landgridge et al. "Transformation of cereals via Agrobacterium and pollen pathway: a critical assessment." vol. 2(4) pp. 631-638 (1992).

* cited by examiner

METHOD FOR TRANSFORMING MONOCOTYLEDONS

CROSS-REFERENCE TO THE RELATED APPLICATIONS

This application is a continuation of application Ser. No. 08/668,464, filed Jun. 25, 1996, now abandoned, which is a Continuation-in-Part of U.S. application Ser. No. 08/193,058 filed on May 3, 1994, issued Jan. 7, 1997 as U.S. Pat. No. 5,591,616, which claims priority as a 371 under the Patent Cooperation Treaty on International Application No. PCT/JP93/00925 filed on Jun. 7, 1993. The entire contents of both of these applications are hereby incorporated by reference.

TECHNICAL FIELD

The present invention relates to a method for transforming monocotyledonous plants ("monocots").

BACKGROUND ART

Conventional methods for transforming monocots include electroporation, the polyethylene glycol method (PEG method), the particle gun method and so on.

The electroporation method is a method in which protoplasts and the desired DNA are mixed, and holes are formed in the cell membranes by electric pulse(s) so as to introduce the DNA into the cells, thereby transforming the cells. This method currently has the highest reproducibility of the conventional methods and various genes have been introduced into monocots, especially into rice plants by this method (Toriyama K. et al., 1988; Bio/Technol. 6:1072–1074, Shimamoto K. et al., 1989; Nature 338: 274–276, Rhodes C. A. et al., 1989; Science 240:204–207). However, this method has the problems that 1) it can be applied only to plant species for which a system for regenerating plants from protoplasts has been established, 2) since it takes several months to regenerate plants from the protoplasts, a long time is required to obtain transformants, and 3) since the culture period is long, the frequency of emergence of mutants during culture is accordingly high, so that the probability of obtaining normal transformants is decreased.

The PEG method is a method in which the desired gene and protoplasts are mixed and the mixture is treated with PEG, thereby introducing the gene into the protoplasts. This method is different from the electroporation method in that PEG is used instead of electric pulses. The efficiency of introducing the gene is thought to be somewhat lower than by the electroporation method. Although there is a report that transformants were obtained by this method, this method is not widely used. Since protoplasts are used, this method has the same problems as the electroporation method (Zhang W. et al., 1988; Theor. Appl. Genet. 76:835–840, Datta S. K. et al., 1990; Bio/Technol. 8:736–740).

The particle gun method is a method in which the desired gene is attached to fine metal particles and the metal particles are shot into cells or tissues at a high speed, thereby carrying out the transformation. Thus, according to this principle, transformation may be performed on any tissues. Therefore, this method is effective for transforming plant species for which a system for regenerating plants from protoplasts has not been established. The efficiency of transformation varies depending on the selection method after the gene was shot into the plant cells. There are no data which compare the efficiency of this method with that of the electroporation method (Gordon-Kamm W. J. et al., 1990; Plant Cell 2:603–618, Fromm M. E. et al., 1990; Bio/Technol. 8:833–839, Christou P. et al., 1991; Bio/Technol. 9:957–962).

Other methods for transforming plants include 1) culturing seeds or embryos with DNA (Topfer R. et al., 1989; Plant Cell 1:133–139, Ledoux L. et al., 1974 Nature 249:17–21); 2) treatment of pollen tubes (Luo and Wu 1988; Plant Mol. Biol. Rep. 6:165-), 3) a liposome method (Caboche M. 1990; Physiol. Plant. 79:173–176, Gad A. E. et al., 1990: 177–183) and 4) a microinjection method (Neuhaus G. et al., 1987; Theor. Appl. Genet. 75:30–36). However, these methods have problems in the efficiency of transformation, reproducibility or applicability, so that these methods are not commonly used.

On the other hand, a method for introducing a gene using the Ti plasmid of bacteria belonging to the genus *Agrobacterium* as a vector is widely used for transforming dicotyledonous plants ("dicots") such as tobacco, petunia, rape and the like. However, it is said that the hosts of the bacteria belonging to genus *Agrobacterium* are restricted to dicots and that monocots are not infected by *Agrobacterium* (De Cleene M. 1976; Bot. Rev. 42:389–466).

As for transformation of monocots by *Agrobacterium*, although transformation of asparagus (Bytebier B. et al., 1987: Proc. Natl. Acad. Sci. USA, 84:5345–5349) and of *Dioscorea bulbifera* (Schafew et al., 1987; Nature 327: 529–532) has been reported, it is said that this method cannot be applied to other monocots, especially to plants belonging to family Gramineae (Potrykus I. 1990; Bio/Technol. 8:535–543).

Grimsley et al. (1987: Nature 325:177–179) reported that T-DNA of *Agrobacterium* in which DNA of maize streak virus was inserted was inoculated to the apical meristem of maize plants and infection of the plants by maize streak virus was confirmed. Since infection symptoms were not observed when the DNA of only the maize streak virus was inoculated, they interpreted the above-mentioned result as a piece of evidence showing that *Agrobacterium* can introduce DNA into maize. However, since it is possible that a virus replicates even if it is not incorporated into the nuclear genome of the plant cell, their result does not show that any T-DNA was incorporated into the nucleus. They subsequently reported that the infection efficiency is the highest when the virus is inoculated to the apical meristem in the shoot apex of the maize (Grimsley et al., 1988: Bio/Technol. 6:185–189), and that the virC gene in the plasmid of *Agrobacterium* is indispensable to the infection (Grimsley et al., Mol. Gen. Genet. 217:309–316).

Gould J. et al. (1991; Plant Physiol. 95:426–434) inoculated super-virulent *Agrobacterium* EHA1 having a kanamycin-resistance gene and a GUS gene to shoot apices of maize after injuring the shoot apices with a needle, and selected for kanamycin resistant shoot apices. As a result, plants having resistance to kanamycin were obtained. They confirmed by Southern blotting analysis that some of the seeds of the subsequent generation of the selected plants had the introduced gene (a so-called "chimera phenomenon").

Mooney P. A. et al., (1991; Plant Cell, Tissue, Organ Culture 25:209–218) tried to introduce kanamycin-resistant gene into embryos of wheat using *Agrobacterium*. The embryos were treated with an enzyme to injure the cell walls, and then *Agrobacterium* was inoculated. Among the treated calli, although very small number of calli which were assumed to be transformants grew, plants could not be regenerated from these calli. The existence of the kanamycin-resistance gene was checked by Southern blotting analysis. In all of the resistant calli, change in the structure of the introduced gene was observed.

Raineri et al. (1990; Bio/Technol. 8:33–38) inoculated super-virulent *Agrobacterium* A281 (pTiBo542) to 8 varieties of rice after injuring the scutella of the rice plants. Growth of tumor-like tissues was observed in two varieties, Nipponbare and Fujisaka 5. Further, an *Agrobacterium* containing a plasmid having a T-DNA from which a hormone-synthesizing gene was removed and instead, a kanamycin-resistance gene and GUS gene were inserted therein was inoculated to embryos of rice. Growth of kanamycin-resistant calli was observed. Although expression of the GUS gene was observed in these resistant calli, transformed plants could not be obtained from the calli. Raineri et al. interpreted these results as showing that the T-DNA was introduced into rice cells.

Thus, although experimental results which suggest that introduction of genes into the plants belonging to family Gramineae such as rice, maize and wheat can be attained by using *Agrobacterium* have been reported, results fully convincing of reproducibility, introduction efficiency and confirmation of the introduction of the gene have not been obtained (Potrykus I. 1990; Bio/Technol. 8:535–543).

As mentioned above, introduction of genes into plants belonging to family Gramineae is now mainly carried out by the electroporation method. However, with this method, since protoplasts are used, a long time and much labor are required to obtain regenerated plants. Further, there is a danger that mutants may emerge at a high frequency due to the long culturing period. Still further, this method cannot be applied to plants such as maize for which a system for regenerating plants from protoplasts has not been established. In view of this, as mentioned above, as for maize, it has been tried to use the apical meristem. However, the operation for isolating the apical meristem requires much labor and it is not easy to prepare apical meristem in a large amount.

DISCLOSURE OF THE INVENTION

Accordingly, an objective of the present invention is to provide a method for transforming monocots, with which the time required for obtaining regenerated plants from the time of transformation is shorter than that in the conventional methods, which can be generally applied even to the plants for which the systems for regenerating plants from protoplasts have not yet been established, and with which the preparation of the materials to be used is easy.

The present inventors intensively studied the influences of the monocotyledonous plant tissues treated with *Agrobacterium*, treatment conditions of *Agrobacterium*, constitution of the binary vector and the like on the introduction efficiency of genes to discover that cultured tissues of monocots can be transformed by using *Agrobacterium* with dramatically high efficiency and reproducibility and that by employing this method, the above-mentioned object can be attained, thereby completing the present invention.

That is, the present invention provides a method for transforming a monocot, comprising contacting a cultured tissue of said monocot during dedifferentiation thereof obtained by culturing an explant on a dedifferentiation-inducing medium for less than 7 days with a bacterium belonging to the genus *Agrobacterium* containing a super binary vector having the virulence region of Ti plasmid pTiBo542 contained in *Agrobacterium tumefaciens* A281, left and right border sequences of T-DNA of a Ti plasmid or an Ri plasmid of a bacterium belonging to the genus *Agrobacterium*, and a desired gene located between said left and right border sequences. The present invention also provides a method for transforming a monocot, comprising contacting a cultured tissue of said monocot during dedifferentiation thereof obtained by culturing an explant derived from an immature tissue on a dedifferentiation-inducing medium for less than 7 days with a bacterium belonging to the genus *Agrobacterium* containing a desired gene and containing a vector having the virulence region of Ti plasmid contained in *Agrobacterium tumefaciens*.

By the present invention, introduction of foreign genes into monocots such as plants belonging to the family Gramineae, including rice, maize, wheat, barley and the like, with good reproducibility was first achieved. Although methods for transforming monocotyledons using *Agrobacterium* are known, they are not established methods as mentioned above. In contrast, according to the present invention, by inoculating *Agrobacterium* to cultured tissues which have not been employed in the conventional methods, genes can be very easily introduced. In the present invention, since a cultured tissue such as a callus which can be easily prepared is used, the sample materials can be obtained more easily than the conventional method employing the apical meristem. Further, since cultured cells are transformed, the time required for regenerating plants is shorter than in cases where protoplasts are transformed, so that the frequency of mutation is decreased. Further, by employing a super binary vector, introduction of genes with high efficiency into varieties which are difficult to culture, such as a variety of rice, was achieved. Still further, as will be described in the examples below, by employing an appropriate selection method after inoculation, the chimera phenomenon in which the desired gene is introduced chimerically can be decreased.

BEST MODE FOR CARRYING OUT THE INVENTION

The monocots which may be transformed by the method according to the present invention are not restricted and the method according to the present invention may be applied to any monocot, such as rice, maize, barley, wheat, asparagus and the like.

The cultured tissue used in the method of the present invention is a cultured tissue undergoing a dedifferentiation process. The term "cultured tissue during the dedifferentiation process" herein means a tissue which is obtained by culturing an explant on a medium containing a plant growth regulator such as an auxin or a cytokinin for less than 7 days, preferably 1–6 days, which tissue is before the stage that a callus or an adventitious embryo-like tissue is formed. The term "dedifferentiated tissue" herein means a callus or an adventitious embryo-like tissue obtained by culturing an explant in a medium containing a plant growth regulator such as an auxin or a cytokinin. The cultured tissue employed in the present invention may be originated from any part of a plant. For example, cultured tissues originated from scutellum, shoot apex, root, immature embryo, pollen and anther can be employed. The tissue to be cultured may preferably be an immature tissue such as immature embryo. The term "immature" herein means that the tissue has not reached the matured state of the tissue and will mature under conditions which allow the maturation.

Dedifferentiation-inducing media are well-known in the art. For example, a medium containing major inorganic salts and vitamins of N6 medium (Chu C. C. 1987; Proc. Symp. Plant Tissue Culture, Science Press Peking, pp. 43–50), 2 mg/l of 2,4-D, 1 g/l of casamino acid, 30 g/l of sucrose and 2 g/l of Gelrite, or a medium containing inorganic salts and vitamins of LS medium (Linsmaier, E., and Skoog, F. 1965; Physiol. Plant 18:100–127), 100 mg/l of casamino acid, 700 mg/l of proline, 1.5 mg/l of 2,4-D, 20 g/l of sucrose and 2.3 g/l of Gelrite. It should be noted that the cultured tissue employed in the method of the present invention is not necessarily a callus; suspension cultured cells may also be employed.

As the *Agrobacterium* used for the transformation, *Agrobacteria* which are employed for the transformation of dicots can be employed. Many of these *Agrobacteria* contain a vector having a DNA region originated from the virulence region (vir region) of a Ti plasmid originated from *Agrobacterium tumefaciens*. The gene encoding a character which is desired to be given to the plant is inserted into this vector, or exists in a separate plasmid and is inserted into the Ti plasmid in vivo by homologous recombination or the like. The present inventors previously developed a vector containing a DNA region originated from the vir region of Ti plasmid pTiBo542 (Jin S. et al., 1987: J. Bacteriol. 169: 4417–4425) contained in a super-virulent *Agrobacterium tumefaciens* A281 exhibiting extremely high transformation efficiency (Hood E. E. et al., 1984; Bio/Technol. 2:702–709, Hood E. E. et al., 1986; J. Bacteriol. 168:1283–1290, Komari T. et al., 1986; J. Bacteriol. 166:88–94, Jin S. et al., 1987; J. Bacteriol. 169:4417–4425, Komari T. 1989; Plant Science 60:223–229 ATCC37394) (Japanese Laid-open Patent Application (Kokai) No. 4-222527. In this specification, this vector is also called "super binary vector"). That is, super binary vector is a vector having the virulence region of Ti plasmid pTiBo542 contained in *Agrobacterium tumefaciens* A281, left and right border sequences of T-DNA of a Ti plasmid or an Ri plasmid of a bacterium belonging to the genus *Agrobacterium*, and a desired gene located between said left and right border sequences. Such a super binary vector may preferably be employed in the present invention. The above-mentioned virulence region of the super binary vector preferably comprises VirB and VirG regions.

Figure 1:
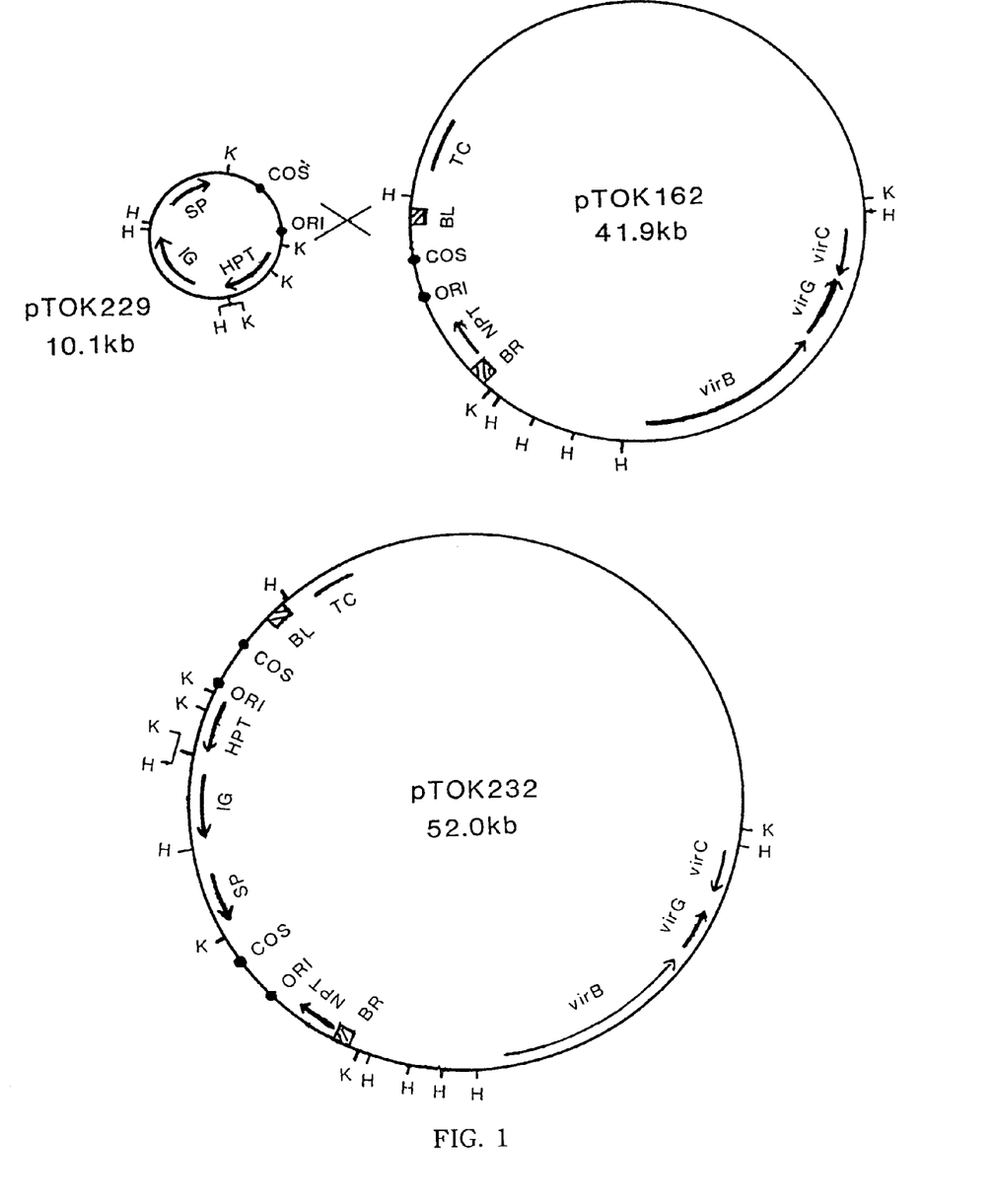
FIG. 1 shows the structure of pTOK162, which is an example of a plasmid contained in *Agrobacterium* bacteria that may be employed in the method of the present invention, and shows the method for constructing a plasmid pTOK232 used in the examples of the present invention.

An example of such a super binary vector is pTOK162 (Japanese Laid-open Patent Application (Kokai) No. 4-222527, EP-A-504,869). The structure is shown in FIG. 1. This plasmid comprises a plasmid called pTOK154 which can replicate in both *Escherichia coli* and in *Agrobacterium tumefaciens*, into which a previously cloned Kpn I fragment (containing virB, virG and virC genes) with a size of 15.2 kb originated from the virulence region of pTiBo542 is inserted. (pTOK154 is a plasmid containing a T region, which was constructed by the method described below from a known plasmid pGA472 derived from the Ti plasmid and a known plasmid having a wide host spectrum called pVCK101.) In pTOK154, between two border sequences of the T region, a kanamycin-resistance gene is inserted as a gene to be introduced into a monocot. This is an example wherein the gene desired to be introduced into the monocot is arranged in a plasmid having the cloned DNA fragment originated from the virulence region of pTiBo542. In FIG. 1, reference symbols represent the following:

SP: spectinomycin-resistance gene
HPT: hygromycin-resistance gene
NPT: kanamycin-resistance gene
TC: tetracycline-resistance gene
IG: "intron GUS" gene
BR: right border sequence of a T-DNA
BL: left border sequence of a T-DNA
virB, virC, virG: vir regions originated from super-virulent *Agrobacterium tumefaciens* A281
ORI: ColE1 replication origin
COS: COS site of λ phage
K: restriction enzyme Kpn I site
H: restriction enzyme Hind III site The gene which is desired to be incorporated into the monocot may be inserted into a restriction site in the T region of the above-described plasmid, and the desired recombinant plasmid may be selected depending on an appropriate selection marker such as drug resistance and the like which the plasmid has. However, if the vector, like pTOK162 shown in FIG. 1, is large and has a number of restriction sites, it is not always easy to insert the desired DNA into the T region of the vector. In such a case, the desired DNA can be inserted into the T region of pTOK162 by utilizing in vivo homologous recombination in cells of *Agrobacterium tumefaciens* (Herrera-Esterella L. et al, 1983; EMBO J. 2:987–995, Horch R. H. et al. Science 1984; 223:496–498). That is, pTOK162 is preliminarily introduced into *Agrobacterium tumefaciens* and the plasmid pBR322 (or a similar plasmid) containing the desired gene is further introduced into *Agrobacterium tumefaciens*. Since pTOK162 has a region homologous with a region of pBR322, the pBR322 derivative containing the desired gene is inserted into pTOK162 by genetic recombination via the homologous regions. Unlike pTOK162, pBR322 cannot replicate by itself in *Agrobacterium tumefaciens*. Therefore, pBR322 can only be maintained in *Agrobacterium tumefaciens* in the form of an insert in pTOK162 (the recombined pTOK162 and pBR322 is hereinafter designated "pTOK162::pBR322 derivative"). By selecting transformants based on selection markers (such as drug resistance) specific to each of pTOK162 and pBR322 derivative, *Agrobacterium tumefaciens* transformants containing pTOK162::pBR322 derivative may be obtained. The present inventors made a study by introducing various plasmids into *Agrobacterium tumefaciens* containing pTOK162, to discover that as the selection marker of the pBR322 derivative, the spectinomycin-resistance gene (SP) originated from transposon Tn7 (De Greve H. H. et al., 1981; Plasmid 6:235–248) is suitable. Thus, in cases where the desired gene has already been cloned into pBR322, by inserting a SP gene into the plasmid, the desired DNA can be inserted into the T region of pTOK162 by homologous recombination in vivo in *Agrobacterium tumefaciens*. Alternatively, a plasmid containing the DNA from pBR322 and a SP gene is first provided, and the desired gene may be inserted into this plasmid. In this case, by utilizing the border sequences of the T region, it is possible to arrange the kanamycin-resistance gene and the desired gene in separate T regions in pTOK162. When plants are transformed using resistance to kanamycin as a marker, there is a substantial probability that both T regions are introduced and the introduction of the desired gene can be sufficiently achieved. Further, in this case, since both T regions may be inserted into different chromosomes, it may be possible to subsequently segregate the desired gene from the kanamycin-resistance gene.

The gene that is desired to be introduced into a monocot is not restricted at all and may be any gene which can give a desired character. Examples of the desired gene include herbicide-resistance genes, antibiotic-resistance genes, virus coat protein genes for giving resistance to the virus, genes related to starch formation in albumen and the like, although the desired genes are not restricted thereto.

As the host bacterium belonging to genus *Agrobacterium*, *Agrobacterium tumefaciens* may preferably be employed, although the host bacterium is not restricted.

Introduction of a plasmid into the bacterium belonging to genus *Agrobacterium* such as *Agrobacterium tumefaciens* can be carried out by a conventional method such as a bacterial triple cross method (Ditta G. et al., 1980; Proc. Natl. Acad. Sci. USA 77:7347–7351).

Since the *Agrobacterium* prepared as mentioned above has a highly virulent DNA originated from pTOK162, transformation of monocots can be achieved with a high efficiency.

It should be noted that in the method of the present invention, although the gene which is desired to be introduced into the monocot is arranged between border sequences of the T region as in the prior art, the desired gene may be arranged in the Ti plasmid or in another plasmid in the *Agrobacterium*. The transformation of the cultured tissue of a monocot by the *Agrobacterium* may be carried out by merely contacting the cultured tissue with the *Agrobacterium*. For example, a cell suspension of the *Agrobacterium* having a population density of $10^6$–$10^{11}$ cells/ml is prepared and the cultured tissue is immersed in this suspension for 3–10 minutes. The resulting cultured tissue is then cultured on a solid medium for several days together with the *Agrobacterium*. Alternatively, transformation may be carried out by adding the *Agrobacterium* to the culture medium of the cultured tissue and continuously culturing the cultured tissue together with the *Agrobacterium*. Thus, in the method of the present invention, the cultured tissue may be subjected to transformation without pretreatment such as treating the cultured tissue with an enzyme or injuring the cultured tissue.

After subjecting the cultured tissues to the transformation, it is preferred to select the transformed cells or transformed tissues state during the dedifferentiation process or in the dedifferentiated state. This can be achieved by culturing the treated tissues on a medium containing a plant growth regulator such as an auxin or a cytokinin, which contains a selectable marker such as hygromycin and an antibiotic against the *Agrobacterium*, that is employed for the selection by the selection marker. The selected cells or the selected tissues may be subjected to regeneration culture by a known method. Thus, plants that have acquired the desired character by the transformation can be regenerated.

The present invention will now be described by way of examples thereof. It should be noted, however, that the present invention is not restricted to the examples.

EXAMPLE 1

(1) Preparation of Sample Cultured Tissues (i) Variety of Rice

Varieties Asanohikari, Tsukinohikari and Koshihikari, which are varieties of japonica rice were selected as samples.

(ii) Scutellum and Scutellum Callus

Mature seeds of rice were sterilized by being immersed in 70% ethanol for 1 minute and then in 1% sodium hypochlorite solution for 30 minutes. The seeds were then placed on 2N6 solid medium (inorganic salts and vitamins of N6 (Chu C. C., 1978; Proc. Symp. Plant Tissue Culture, Science Press Peking, pp. 43–50), 1 g/l of casamino acid, 2 mg/l of 2,4-D, 30 g/l of sucrose, 2 g/l of Gelrite). Scutella were removed from the seeds on Day 4 from the beginning of the culture on 2N6 solid medium and used as "scutellum" samples. On the other hand, after culturing the mature seeds for about 3, weeks, the formed calli originated from scutella were transferred to 2N6 medium and cultured therein for 4–7 days. The resulting calli were used as "scutellum callus" samples.

(ii) Shoot Apex Tissue

Mature seeds of rice were sterilized by the above-described method and were placed on ½ N6 solid medium (half strength of major inorganic salts and minor salts of N6, vitamins of N6, 1 g/l of casamino acid, 20 g/l of sucrose and 2 g/l of Gelrite). From seedlings on Day 3 after germination, tissues of 2–3 mm length containing apex dividing tissues were cut out and used as samples.

(iv) Root Segment and Root Callus

From the seedlings obtained by the method described in (iii), tip portions of 5–10 mm length of the seed roots were cut out and used as "root segment" samples. On the other hand, these radicles were cultured on 2N6 solid medium for about 2 weeks to obtain calli, and these calli were used as "root callus" samples.

(v) Suspended Cultured Cells

The calli originated from scutella were transferred to AA liquid medium (major inorganic salts of AA, amino acids of AA and vitamins of AA (Toriyama and Hinata 1985; Plant Science 41:179–183), MS minor salts (Murashige and Skoog 1962; Physiol. Plant. 15:473–497), 0.5 g/l of casamino acid, 1 mg/l of 2,4-D, 0.2 mg/l of kinetin, 0.1 mg/l of gibberellin and 20 g/l of sucrose) and the cells were cultured therein at 25° C. in the dark with shaking at 120 rpm to obtain suspended cultured cells. The medium was replaced with fresh medium every week. (2) Ti Plasmid (Binary Vector)

A hygromycin resistance gene (HPT) and β-D-glucuronidase (GUS) gene were inserted into the T-DNA region of a Ti plasmid to obtain the following plasmids:

(i) pIG121 Hm:

A plasmid in which the GUS gene containing the first intron of the catalase gene of castor bean ("intron GUS" gene) and a hygromycin-resistance gene were ligated (Nakamura et al., 1991; Plant Biotechnology II (Extra Issue of GENDAI KAGAKU, pp. 123–132); the construct was a gift of Dr. Nakamura of Nagoya University).

(ii) pTOK232

1. Insertion of Intron GUS and Hygromycin-Resistance Genes into Intermediate Vector pTOK229

The Cla I fragment (2.5 kb) of the spectinomycin-resistance gene originated from Tn7 were treated with Klenow fragment to blunt the ends. The resulting fragment was inserted into the Sma I site of pUC19 to obtain a plasmid pTOK107 (5.2 kb) having ampicillin-registance and spectinomycin-resistance genes. The obtained pTOK107 was treated with Eco RI and Hind III and the obtained 2.5 kb fragment containing the spectinomycin-resistance gene was ligated to a Eco RI-Hind III fragment (2.7 kb) of pGA482 to obtain pTOK170 (5.2 kb) containing the spectinomycin-resistance gene and has a Hind III site and a Hpa I site.

A vector pIG221 in which the first intron of catalase of castor bean and a GUS gene ("intron GUS gene") are ligated to a 35S promoter (Ohta S. et al., 1990; Plant Cell Physiol. 31: 805–813, presented by Dr. Nakamura of Nagoya University), was digested with Eco RI and the resultant was treated with Klenow fragment to blunt the ends. A Hind III linker (pCAAGCTTG, code 4660P commercially available from TAKARA SHUZO) was ligated to the resultant. A fragment containing the 35S promoter and intron GUS gene was cut out by digesting the resulting vector with Hind III, and the fragment was inserted into the Hind III site of a plasmid pGL2 (J. Paszkowski, obtained from Friedrich Mieocher Institute) containing a hygromycin-resistance gene ligated to a 35S promoter, to obtain pGL2-IG (7.6 kb). The above-mentioned plasmid pGL2 was obtained by inserting a hygromycin-resistance gene (Gritz L. and Davis J. 1983; Gene 25: 179–188) into pDH51 (Pietrazak et al., 1986; Nucleic Acids Research 14: 5857–5868). The fragment obtained by treating pTOK170 with Hpa I was ligated to a Pvu II fragment (5.2 kb) of pGL2-IG to obtain pTOK229 (10.1 kb).

2) Insertion into Super Binary Vector pTOK162

A super binary vector pTOK162 was obtained by inserting virB, virC and virG genes of strongly virulent *Agrobacterium tumefaciens* A281. Insertion of the desired genes (hygromycin-resistance gene and intron GUS gene) into the binary vector was carried out by homologus recombination. That is, since both vectors contain a region originated from an *E. coli* plasmid pBR322, in the bacterial cells selected by resistances to spectinomycin and kanamycin, only the plasmid generated by recombination of both plasmids is retained. The plasmid obtained by the fact that the hygromycin-resistan gene and the intron GUS gene were inserted into the super binary vector is called pTOK232 (see FIG. 1).

An *E. coli* strain MC1000 harboring the plasmid pTOK162 was deposited under the terms and conditions of the Budapest Treaty on Sep. 30, 2004, at the Incorporated Administrative Agency National Institute of Technology and Evaluation Patent Microorganisms Depositary (NPMD), located at 2-5-8 Kazusakamatari Kisarazu-shi, Chiba-ken 292-0818, Japan, under the accession number Nite BP-24.

(3) Host *Agrobacterium tumefaciens*

Strains LBA4404 and EHA101 in which T-DNA regions were deleted were used as the host bacteria. Strain LBA4404 has a helper plasmid PAL4404 (having a complete vir region), and is available from the American Type Culture Collection (ATCC 37349). Strain EHA101 has a helper plasmid having the vir region originated from a strongly virulent *Agrobacterium tumefaciens* A281, and is available from Hood E. E. et al., 1986.

The various binary vectors described in (2) were introduced into these two strains of *Agrobacterium tumefaciens*, and the following strains described were used for introducing the genes. The plasmids were introduced into the *Agrobacterium* strains by a triple cross (Ditta G. et al., 1980; Proc. Natl. Acad. Sci. USA 77: 7347–7351).

LBA4404(pTOK232)
LBA4404(pIG121Hm)
EHA101(pIG121Hm)

(4) Preparation of Suspension of *Agrobacterium tumefaciens*

Colonies obtained by culturing the *Agrobacterium* strains on AB medium (Drlica K. A. and Kado C. I. 1974; Proc. Natl. Acad. Sci. USA 71:3677–3681) containing hygromycin (50 μg/ml) and kanamycin (50 μg/ml) for 3–10 days were collected with a platinum loop and suspended in modified AA medium (same as the composition of the above-described AA medium except that concentrations of sucrose and glucose were changed to 0.2 M and 0.2 M, respectively, and that 100 μM of acetosyringone was added, pH 5.2). The cell population was adjusted to $3 \times 10^9$–$5 \times 10^9$ cells/ml and the suspensions were used for inoculation.

(5) Inoculation Conditions

The sample tissues were washed with sterilized water and immersed in the above-described suspensions of *Agrobacterium* strains, respectively, for 3–10 minutes. Thereafter, the shoot apex samples were placed on N6S3 solid medium (½ N6 major inorganic salts, N6 minor salts, N6 vitamins, Chu C. C., 1978, AA amino acids (Toriyama and Hinata 1985), 1 g/l of casamino acid, 0.2 mg/l of NAA, 1.0 mg/l of kinetin and 3 g/l of Gelrite) containing 100 μM of acetosyringone, 10 g/l of glucose and 20 g/l of sucrose. The other tissue samples such as scutellum callus samples were cultured on 2N6 solid medium containing acetosyringone, glucose and sucrose in the same concentrations as mentioned above. The co-cultures were carried out at 25° C. in the dark for 2–5 days. The resulting inoculated tissues were then washed with sterilized water containing 250 mg/l of cefotaxime and then the culture was continued on the respective solid media containing the same concentration of cefotaxime as mentioned above.

(6) Method for Examining GUS Activity

Immediately after the above-mentioned culture with the *Agrobacterium* strains, the tissues were immersed in 0.1 M phosphate buffer (pH 6.8) containing 0.1% TRITON X-100 at 37° C. for 1 hour. After washing off the *Agrobacterium* strains with phosphate buffer, phosphate buffer containing 0.1 mM of 5-bromo-4-chloro-3-indolyl-β-D-glucuronic acid and 20% methanol was added to the tissues. After incubation at 37° C. for 24 hours, the number of blue-colored tissues was counted under a microscope and the percentages thereof based on the number of samples are described. For assay of the GUS activities of the plants assumed to be transformants after the selection treatment, leaves were collected from the plants and GUS staining was performed in the same manner. If the entire leaf or the cut face of the leaf is uniformly colored in blue, the plant was judged to be a positive plant, and if the leaf or the cut face of the leaf is chimerically stained, the plant was judged to be a chimera plant.

(7) Selection of Transformed Cells and Tissues (i) Shoot Apex

Shoot apices cultured with the *Agrobacterium* strains for 5 days were cultured on N6S3 medium containing 250 mg/l of cefotaxime for 2 weeks. The grown shoot apex tissues were transplanted to N6S3 medium containing 40 mg/l of hygromycin and selection of the transformants was carried out.

(ii) Scutellum

Scutella cultured with the *Agrobacterium* strains for 3 days were cultured on 2N6 medium containing 250 mg/l of cefotaxime for 1 week. Selection of transformed cells were then carried out on 2N6 medium containing 50 mg/l of hygromycin.

(iii) Cultured Tissue (Scutellum Callus)

Tissues cultured with the *Agrobacterium* strains for 3 days were cultured on 2N6 medium containing 250 mg/l of cefotaxime for 1 week. Hygromycin-resistant cultured tissues were selected by culturing the cultured tissues on 2N6 medium containing 50 mg/l of hygromycin for 3 weeks (primary selection). The obtained resistant tissues were further cultured on N6-12 medium (N6 inorganic salts, N6 vitamins, 2 g/l of casamino acid, 0.2 mg/l of 2,4-D, 0.5 mg/l of 6BA, 5 mg/l of ABA, 30 g/l of sorbitol, 20 g/l of sucrose and 2 g/l of Gelrite) containing 50 mg/l of hygromycin for 2–3 weeks (secondary selection), and the calli grown on this medium were transferred to a plant regeneration medium N6S3 containing 0, 20 or 50 mg/l of hygromycin. In all of the media used after the culture with *Agrobacterium* strains, cefotaxime was added to 250 mg/l.

(iv) Suspended Cultured Cells

The cells cultured with the *Agrobacterium* strains for 5 days were cultured in 2N6 medium containing 250 mg/l of cefotaxime for 1 week, and then the selection of the transformed cells was carried out on 2N6 medium containing 50 mg/l of hygromycin.

(8) Expression of Introduced Genes in the Progeny of Transformants

Seeds of the progeny of the transformants were sown in aqueous 400-fold Homai hydrate (Kumiai Kagaku Inc.) solution containing 70 mg/l of hygromycin and incubated therein at 25° C. for 10 days, thereby examining the resistance to hygromycin. Twenty seeds of each plant of the progeny of the transformants were sown and cultured for about 3 weeks. Leaves were collected from the obtained seedlings and examined for the expression of the GUS gene.

(9) Analysis of Introduced Genes by Southern Blotting Method

DNAs were extracted from the primary transformants of varieties Asanohikari and Tsukinohikari by the method of Komari et al. (Komari et al., 1989; Theoretical and Applied Genetics 77: 547–552), and the DNAs were treated with the restriction enzyme Hind III. The resulting fragments were subjected to detection of the introduced genes by Southern blotting analysis using the HPT gene as a probe. The length of the Hind III fragment containing the HPT gene as a probe is about 5.5 kb and the length of the DNA region from the Hind III site in the T-DNA in this region to the L border sequence is about 5.4 kb (FIG. 1). The Southern blotting analysis was carried out as describe in "Molecular Cloning: A Laboratory Manual" (Sambrook et al., 1989; Cold Spring Harbor Laboratory Press). Two GUS positive plants, two GUS negative plants and two hygromycin-resistant plants were picked up from each of the two lines of the progeny of transformants of Tsukinohikari and were subjected to the Southern blotting analysis in the same manner as mentioned above.

(10) Differences in Efficiencies of Introducing Genes Depending on Sample Tissues (Expression of GUS after Culturing with *Agrobacterium* Strains)

In order to confirm that *Agrobacterium* can introduce genes into cells of monocots, various tissues of the rice variety Tsukinohikari were treated with *Agrobacterium tumefaciens* EHA101 having a super-virulent vir region, into which the binary vector (supra) containing the hygromycin-resistance gene and the GUS gene were introduced, and then the GUS activities were examined. The sample tissues were shoot apices, radicles, scutella, radicle calli, scutellum calli and suspended: cultured cells. In cases where the tissues were not treated with the *Agrobacterium* strain, no tissues exhibited GUS activity as indicated by blue color. On the other hand, in cases where the tissues were treated with *Agrobacterium tumefaciens* EHA101 (pIG121Hm), expression of GUS was confirmed in all of the tissues except for radicles. The ratio of the number of the tissues showing blue color to the number of treated tissues was the highest in scutellum calli (Table 1). Further, the size of the tissues expressing GUS was also largest in scutellum calli. The tissues exhibiting the second highest rate of introduction next to the scutellum calli were shoot apices. Further, while the scutellum calli and the suspension cells which are dedifferentiated tissues of scutella exhibited a high introduction rate, the introduction rate in scutella was apparently lower. This suggests that genes are more easily introduced into tissues having high cell-dividing activities.

TABLE 1

Differences in Efficiency of Introduction of GUS Gene Depending on Sample Material
(Variety: *Tsukinohikari*)

| Sample Tissue | Number of GUS+ Tissues/ Number of Sample Tissues (%) | | Size of GUS-stained Portion Based on Treated Tissue |
|---|---|---|---|
| | Non-Treated Group | Treated Group | |
| Shoot Apex | 0/30(0) | 109/157(69) | +++ |
| Root Segment | 0/20(0) | 0/30(0) | |
| Root Callus | 0/30(0) | 24/115(21) | + |
| Scutellum | 0/50(0) | 8/89(9) | + |
| Scutellum Callus | 0/141(0) | 312/395(79) | +++ |
| Suspension Cells | 0/232(0) | 61/247(25) | ++ |

+: 1% or less, ++: 1~10%, +++: 10% or more

It has been confirmed that the binary vector pIG121Hm used in this experiment does not express GUS gene in *Agrobacterium* cells because the intron of castor bean plant is inserted in the promoter of the GUS gene (Nakamura et al., 1991). Thus, from the results of the experiments described above in which the expression of the GUS gene after the culturing with *Agrobacterium* is used as an index, it was confirmed that genes can be introduced into rice cells by *Agrobacterium*.

(11) Differences in Rate of Emergence of Transformed Tissues and Cells Depending on Sample Tissues Selection of transformed tissues and transformed cells was carried out according to the resistance to hygromycin, using shoot apices, scutella, scutellum calli and suspension cells after the culture with the *Agrobacterium* strain. As a result, growth of transformants exhibiting resistance to hygromycin were observed in scutellum calli and the suspension cells (Table 2). Further, all of the selected cells expressed the GUS gene. Although the shoot apex tissues exhibited high rate of introduction of GUS gene after the culture with the *Agrobacterium* strain, after the selection by hygromycin, all tissues died and no tissues resistant to hygromycin were obtained. Although shoot apex is a tissue containing the apical meristem, in order that cells expressing a hygromycin-resistance continue to grow after the treatment for introducing the gene, it is necessary that the gene be introduced into the limited apical meristem. The reason why no resistant tissues were obtained in spite of the fact that a number of genes were introduced into the shoot apices after the culture with the *Agrobacterium* strain is thought to be that the probability that the gene is introduced in the vicinity of the apical meristem is low. Further, it is easily assumed that even if a gene is introduced in the vicinity of the apical meristem so that transformed cells are obtained, the possibility that the obtained plants exhibit chimeric properties is high. Therefore, it is thought that the transformation method utilizing shoot apex, which was reported by Gould et al (1991), has more technical difficulties and less reproducibility than the method utilizing a dedifferentiated tissue such as callus.

While transformed cells were obtained from the scutellum calli and the suspension cells which were originated from scutella of mature seeds, resistant cells were not obtained from the scutellum samples. Although the introduction of the genes was tried by using injured scutella in accordance with the teachings by Raineri et al. (1990), the efficiency of introducing genes was not increased and no transformed cells were obtained. In contrast, in cases where scutellum calli were used as the samples, transformed cells were obtained with good reproducibility and high frequency, without a treatment such as injuring the samples. From these observations, it is thought that cultured tissues which were dedifferentiated or which are in the process of dedifferentiation are suited as tissues to be subjected to transformation by *Agrobacterium*.

TABLE 2

Differences in Rate of Energence of Transformed Tissues and Cells Depending on Sample Material
(Variety: *Tsukinohikari*)

| Sample Tissue | Number of Hygromycin-resistant Tissues/ Number of Treated Tissues (%) | |
|---|---|---|
| | Non-Treated Group | Treated Group |
| Shoot Apex | 0/20(0) | 0/77(0) |
| Scutellum | 0/30(0) | 0/128(0) |
| Scutellum Callus | 0/50(0) | 169/743(23) |
| Suspension Cells | 0/250(0) | 22/254(9) |

(12) Differences in Efficiencies of Introducing Genes Depending on Varieties of Rice (Expression of GUS after Culturing with *Agrobacterium* Strains)

There are large differences among varieties in the conditions for establishing cultured cells and for regenerating plants from the cultured cells (Mikami and Kinoshita 1988; Plant Cell Tissue Organ Cult. 12:311–314). It is said that, among the Japonica rices, Koshihikari is difficult to culture. On the other hand, Tsukinohikari employed in the preceding section is relatively easy to culture. When using the transformation method utilizing *Agrobacterium*, it is practically inconvenient if such differences among varieties exist. In order to clarify this point, the differences in the efficiencies of gene introduction between Koshihikari and Tsukinohikari which have different ease of culture were examined. The sample tissues employed were scutellum calli and the *Agrobacterium tumefaciens* strains employed were EHA101 (pIG121Hm) and LBA4404(pIG121Hm).

While GUS activity was observed in not less than 90% of calli of Tsukinohikari in each experiment, GUS activity was observed in Koshihikari at lower rates (Table 3). Thus, in cases where EHA101(pIG121Hm) or LBA4404 (pIG121Hm) is used, there is a difference in the introduction efficiency between the varieties.

TABLE 3

Differences in Rate of Introduction of GUS Gene Depending on Agrobacterium Strain and Rice Variety

| | | Number of GUS+ Tissues/Number of Treated Tissues (%) | | |
|---|---|---|---|---|
| | | Strain | | |
| Variety | Experiment | LBA4404 (pIG121Hm) | EHA101 (pIG121Hm) | LBA4404 (pTOK232) |
| *Tsukinohikari* | 1 | 67/70(96) | 78/87(90) | 64/66(97) |
| *Tsukinohikari* | 2 | 72/86(84) | 68/73(93) | 82/82(100) |
| *Koshihikari* | 1 | 46/135(34) | 43/116(37) | 124/131(95) |
| *Koshihikari* | 2 | 28/107(26) | 81/143(57) | 102/103(99) |

(13) Differences in Efficiencies of Introducing Genes Depending on *Agrobacterium* Strains (Expression of GUS Gene after Culturing with *Agrobacterium* Strains)

EHA101(pIG121Hm) has a helper plasmid containing the vir region of super-virulent *Agrobacterium tumefaciens* A281. LBA4404(pIG121Hm) has an ordinary vir region. On the other hand, although the vir region of the helper plasmid in LBA4404(pTOK232) is ordinary, a gene which is a part of the vir region of the super-virulent *Agrobacterium tumefaciens* A281 is contained in the binary vector. This binary vector is originated from pTOK162 and made it possible to transform at a very high rate dicotyledonous species which are difficult to transform (Saito Y. et al., 1992; Theor. Appl. Genet. 83:679–683). Thus, there is a possibility that the transformation efficiency is largely influenced by the existence a super-virulent vir region or by the manner of existence thereof. Thus, using the above-described three *Agrobacterium* strains whose vir regions are different, the efficiencies of introducing GUS gene were compared. The samples used were scutellum calli of Koshihikari and Tsukinohikari.

Even with LBA4404(pIG121Hm) which does not have a super-virulent vir region, tissues exhibiting GUS activities were obtained in both varieties. However, in Koshihikari, the rate was as low as about 30%. With EHA101 (pIG121Hm) having the super-virulent vir region in the helper plasmid, the introduction efficiency in Koshihikari was somewhat higher. With LBA4404(pTOK232) having the super-virulent vir region in the binary vector, GUS activities were observed in not less than 95% tissues even with Koshihikari as with Tsukinohikari (Table 3). Further, as for the area of blue-colored regions in each tissue, the area was the largest with LBA4404(pTOK232), which indicates a high introduction efficiency.

(14) Differences in Selection Efficiency Depending on Strains (Hygromycin-Resistant Callus)

Using the above-mentioned 3 strains, the selection rates of hygromycin-resistant calli after culturing scutellum calli of Tsukinohikari and Koshihikari with the *Agrobacterium* strains were compared. As for the rate of emergence of the resistant calli, LBA4404(pTOK232) exhibited the highest rate. No differences about the rate of selection were observed between the varieties (Table 4). With the strains LBA4404(pIG121Hm) and EHA101(pIG121Hm), the rates of selection were low. Especially, with Koshihikari which is difficult to culture, the rate of emergence of hygromycin-resistant calli was as low as about 2%. Thus, it is thought that LBA4404(pTOK232) having a part of the super-virulent vir gene in the binary vector is the best as the *Agrobacterium* strain used for transforming rice.

TABLE 4

Differences in Transformation efficiency Depending on Agrobacterium Strain (Scutellum Callus)

Number of Hygromycin-resistant Callus/Number of Treated Callus (%) Strain

| Variety | Experiment | LBA4404 (pIG121Hm) | EHA101 (pIG121Hm) | LBA4404 (pTOK232) |
|---|---|---|---|---|
| Tsukinohikari | 1 | 91/338(27) | 139/301(46) | 169/305(55) |
| Tsukinohikari | 2 | 59/421(14) | 66/425(16) | 110/360(31) |
| Tsukinohikari | 3 | | 10/521(2) | 174/644(27) |
| Tsukinohikari | 4 | | 20/349(6) | 100/349(29) |
| Koshihikari | 1 | 6/269(2) | | 65/283(23) |

(15) Manner of GUS Gene Expression in Hygromycin-Resistant Transformants

The thus obtained resistant calli were subjected to secondary selection, and plants were regenerated from the selected resistant calli. A group in which hygromycin was not added to the N6S3 medium for regeneration was provided. In this group, a number of plants which did not exhibit GUS activity or which exhibited GUS activity chimerally emerged. However, in cases where hygromycin was added to the regeneration medium, the number of these plants greatly decreased and the number of plants, each of which exhibits GUS activity in the whole plant, was increased (Table 5, Table 6 and Table 7). In cases where the tissue was not treated with *Agrobacterium*, no plants which exhibited resistance to hygromycin or GUS activity were obtained. Therefore, the plants each of which exhibited GUS activity in the whole plant and which was regenerated from hygromycin-resistant callus, are considered as transformants.

TABLE 5

Expression of GUS Gene in Plants Regenerated from Hygromycin-resistant Calli (Variety: *Asanohikari*)

| Resistant Callus | Number of Regenerated Plants | Expression of GUS Gene | | |
|---|---|---|---|---|
| | | Stably Positive | Chimera | Negative |
| 1 | 26 | 25 | 1 | 0 |
| 2 | 8 | 7 | 1 | 0 |

(Hygronycin was added to culture medium until regeneration of plants.)

Table 6 and Table 7

TABLE 6

Expression of GUS Gene in Plants Regenerated from Hygromycin-resistant Calli (Variety: *Tsukinohikari*)

| | Number of Lines | | |
|---|---|---|---|
| Sample Strain | Sample Hygromycin-resistant Calli | Calli Yielded Regenerated Plants | GUS Positive Regenerated Plants |
| LBA4404(pIG121Hm) | 3 | 1 | 1 |
| EHA101(pIG121Hm) | 20 | 17 | 10 |
| LBA4404(pTOK232) | 20 | 15 | 12 |

(Hygromycin was added to culture medium until regeneration of plants.)

TABLE 7

Expression of GUS Gene in Plants Regenerated from Hygromycin-resistant Calli (Variety: *Asanohikari*)

| | Number of Lines | | |
|---|---|---|---|
| Sample Strain | Sample Hygromycin-resistant Calli | Calli Yielded Regenerated Plants | GUS Positive Regenerated Plants |
| LBA4404(pIG121Hm) | 19 | 5 | 3 |
| EHA101(pIG121Hm) | 11 | 4 | 1 |
| LBA4404(pTOK232) | 19 | 11 | 11 |

(Hygromycin was added to culture medium until regeneration of plants.)

(16) Ploidy and Fertility of Seeds of Transformants

When cultivated in a green house, the thus obtained transformants exhibited normal growth and morphology and no plants exhibited characteristics of tetraploidy or malformation. As for the fertility of the seeds, although some plants exhibited partial infertility or complete infertility, most plants exhibited substantially normal fertility.

(17) Expression and Analysis of Introduced Genes in the Primary Transformants and in the Progeny Fragments obtained by Hind III digesting the whole DNAs in the primary transformants were subjected to detection of the introduced gene by Southern blotting analysis using the HPT gene as a probe. In all of the tested plants, the existence of the introduced gene in a number of one to several copies was confirmed (Table 8 and Table 9). While the size of the Hind III fragment containing the HPT gene in plasmid pTOK232 is 5.5 kb, in all of the tested transformants, a band having a size larger than about 6 kb was observed. This demonstrates that the T-DNA was incorporated into the plant chromosomes. The fact that the size of the detected DNA fragment differed from plant to plant indicates that the site in which the HPT gene was introduced was different from transformant to transformant. Therefore, it was confirmed that the fact that the introduced gene was detected was not due to the *Agrobacterium* bacteria remaining in the plants.

The resistance to hygromycin of the progeny of the transformants was examined. With the seeds of control plants, substantially no germination was observed or the growth after germination was severely inhibited. In contrast, many of the seeds obtained from the transformants exhibited normal germination and growth (Tables 8 and 9). These hygromycin-resistant plants also expressed the GUS gene. In many lines, expression of the hygromycin resistance and the GUS genes, genetically segregated substantially in accordance with one factor segregation. As for transformant lines 1–2 and 3–2 of Asanohikari in Table 8, existence of 2 or more factors of introduced genes is expected from the segregation ratio. The results of Southern blotting analysis were also compatible with two factor segregation. In the transformant 2-1 in Table 8, existence of two copies of the introduced genes was confirmed. One of these bands represents a fragment shorter than 5 kb, so that it is assumed that a T-DNA of an incomplete form was incorporated. It is assumed that because of this, this transformant exhibited segregation like one factor segregation of the hygromycin resistance in the progeny.

As shown in Table 9, many of the transformants of Tsukinohikari exhibited one factor segregation of the hygromycin resistance and of the GUS gene in the progeny. However, Southern blotting analysis of the primary transformant revealed that most of the transformants contained a plurality of copies of the gene although some of them contained a single copy of the gene. The progeny of the transformant 18a which contained one copy of the introduced gene and the progeny of the transformant 16c which contained two copies of the introduced gene were subjected to Southern blotting analysis. Two plants each of the GUS positive, GUS negative and hygromycin-resistant plants of each line were subjected to the analysis. As a result, in all of the plants except for the GUS negative plants, the same bands as detected in the plants of the primary transformants were detected. Therefore, it was shown that the introduced genes were inherited to the subsequent generations. As for the line 16c having two copies of the introduced gene, the fact that both the progeny of GUS positive plants and hygromycin-resistant plants had the same two copies of the introduced genes suggests that a plurality of genes were incorporated into the same chromosome or the same locus.

These results indicate that the genes introduced into rice plants by *Agrobacterium* were incorporated in the nuclei of the plant cells and were inherited to the subsequent generations in accordance with Mendel's laws.

TABLE 8

Number of Copies of Introduced Genes in Transformants Determined by Southern Blotting Analysis and Expression of Introduced Gene in the Progeny of Transformants (Variety: *Asanohikari*)

| | | Number of Plants of the Progeny of Transformants | | | |
|---|---|---|---|---|---|
| | Number of Copies of Introduced | Resistance to Hygromycin | | Expression of GUS | |
| Transformants | Gene | Resitant | Sensitive | Positive | Negative |
| Control | — | 0 | 60 | 0 | 20 |
| 1–2 | 2 | 30 | 0 | 19 | 1 |
| 2–1 | 2* | 64 | 26 | 13 | 5 |
| 3–2 | 2 | 59 | 1 | 19 | 1 |

*In one of the two copies of the introduced genes, the restriction fragment was short, so that the introduced gene was incomplete.

TABLE 9

Number of Copies of Introduced Genes in Transformants Determined by Southern Blotting Analysis and Expression of Introduced Gene in the Progeny of Transformants (Variety: *Tsukinohikari*)

| | | Number of Plants of the Progeny of Transformants | | | |
|---|---|---|---|---|---|
| | Number of Copies of Introduced | Resistance to Hygromycin | | Expression of GUS | |
| Transformants | Gene | Resitant | Sensitive | Positive | Negative |
| Control | — | 0 | 60 | 0 | 20 |
| 1 | 1 | 46 | 26 | 15 | 5 |
| 2a | 2 | 33 | 18 | 13 | 5 |
| 2b | 2 | 31 | 9 | 15 | 5 |
| 3 | 2 | 29 | 10 | 16 | 3 |
| 4a | 3 | 22 | 21 | 13 | 7 |
| 4b | 3 | 48 | 11 | 16 | 3 |
| 5a | 3 | 26 | 13 | 17 | 3 |
| 5b | 3 | 36 | 14 | 17 | 3 |
| 5c | 3 | 24 | 9 | 17 | 2 |
| 6 | 2 | 47 | 13 | — | — |
| 7 | 1 | 56 | 20 | 14 | 5 |
| 8 | 4 | 45 | 22 | — | — |
| 9 | 1 | 52 | 18 | 18 | 2 |
| 10 | 4 | 53 | 10 | — | — |
| 11 | 2 | 75 | 15 | 18 | 2 |
| 12 | 3 | 44 | 7 | 14 | 6 |
| 13a | 2 | 33 | 18 | 15 | 5 |
| 13b | 2 | 32 | 8 | 13 | 7 |
| 14a | 1 | 72 | 20 | 15 | 5 |
| 14b | 1 | 26 | 14 | 10 | 10 |
| 15 | 1~2 | 22 | 7 | 12 | 8 |
| 16a | 2 | 31 | 10 | 15 | 2 |
| 16b | 2 | 32 | 8 | 14 | 3 |
| 16c* | 2 | 69 | 24 | 13 | 7 |
| 17 | 6 | 89 | 41 | — | — |
| 18a* | 1 | 35 | 5 | 15 | 5 |
| 18b | 1 | 70 | 20 | 10 | 10 |
| 19 | 2 | 47 | 13 | — | — |

*Introduced genes in plants of the next generation were analyzed by Southern blotting analysis.

EXAMPLE 2

(1) Maize Varieties

Maize varieties A188, F1 (A188×Black Mexican Sweet), F1 (A188×B73Ht), F1 (B73Ht×A188) and F1 P3732 were selected as the sample materials. The varieties of A188, Black Mexican Sweet and B73Ht were obtained from the National Institute of Agrobiological Resources, Ministry of Agriculture, Forestry & Fisheries, and P3732 was obtained from IWATA RAKUNOU KYODOKUMIAI.

(2) Preparation of Tissues in the Vicinity of the Growth Point

Mature seeds were immersed in 70% ethanol for 1 minute and in 1% sodium hypochlorite for 5 minutes. The seeds were then washed three times with sterilized water and were placed on LS solid medium (inorganic salts and vitamins of Linsmaier and Skoog; Linsmaier, E. and Skoog, F. 1965; Physiol. Plant 18: 100–127, 100 mg/l of casamino acid, 700 mg/l of proline, 20 g/l of sucrose and 2.3 g/l of Gelrite). After culturing the seeds at 25° C. in the dark for 4 days, tissues with a length of about 0.1×0.3 mm containing the apex dividing tissues were cut out and used as samples.

(3) Preparation of Calli Originated from Immature Embryos

Immature embryos were placed on LSD1.5 solid medium (inorganic salts and vitamins of Linsmaier and Skoog, 100 mg/l of casamino acid, 700 mg/l of proline, 1.5 mg/l of 2,4-D, 20 g/l of sucrose and 2.3 g/l of Gelrite). After culturing the embryos for 3 weeks, the formed calli originated from scutella were collected and used in the subsequent experiments.

(4) Strains of *Agrobacterium*

Among the strains of *Agrobacterium* described in Example 1, LBA4404(pTOK232) and EHA101 (pIG121Hm) were used.

(5) Preparation of Suspensions of *Agrobacterium* Strains

Colonies of the *Agrobacterium* strains obtained by culturing the *Agrobacterium* strains on AB medium containing hygromycin (50 mg/l) and kanamycin (50 mg/l) for 3–10 days were collected using a platinum loop and the cells were suspended in the modified AA medium described in Example 1. The cell population was adjusted to $3 \times 10^9$–$5 \times 10^9$ cells/ml and the resultants were used for inoculation.

(6) Conditions for Inoculation to Tissues in the Vicinity of the Growth Point and for Culturing After piercing the cut out tissues with a glass needle, the sample tissues were immersed in the above-described suspensions of the *Agrobacterium* strains for 3–10 minutes. The tissues were then transferred to modified LS solid medium (inorganic salts of Linsmaier and Skoog, vitamins of Murashige and Skoog; Murashige, T. and Skoog, F. 1962; Physiol. Plant. 15:473–497, 0.1 mg/l of kinetin, 1.0 mg/l of casamino acid and 2.3 g/l of Gelrite) and were cultured at 25° C. under illumination for 2–3 days. Thereafter, the tissues were washed with sterilized water containing 250 mg/l of cefotaxime and then the culture was continued on LS solid medium containing the same concentration of cefotaxime.

(7) Conditions for Inoculation to Calli and for Culturing

The calli were immersed in the above-described *Agrobacterium* suspensions for about 5 minutes and the resulting calli were transferred to 2N6 solid medium containing acetosyringone described in Example 1 at 25° C. in the dark for 3 days to carry out the culture with the *Agrobacterium* strains. The calli were washed with sterilized water containing 250 mg/l of cefotaxime and then the culture was continued on LSD1.5 solid medium containing the same concentration of cefotaxime and 30 mg/l of hygromycin, thereby carrying out the selection of transformed calli.

(8) Method for Examining GUS Activity

The shoot apex tissues and the calli immediately after the culture with the *Agrobacterium* strains and the shoot apex tissues and the calli which were continuously cultured after the culture with the *Agrobacterium* strains were examined for their GUS activities by the method described in Example 1.

(9) Introduction of Genes into Shoot Apex Tissues

In order to confirm that transformation employing the growth point tissues (shoot apex tissues) reported by Gould et al (Gould J. et al., 1991; Plant Physiol. 95:426–434) can be achieved, isolated shoot apex tissues were treated with the above-described *Agrobacterium tumefaciens* strain EHA101(pIG121Hm), and the GUS activities of the grown plants were examined. While expression of the GUS gene was not observed in the tissues which were not treated with the *Agrobacterium* strain, expression of the GUS gene was observed in the spots pierced with the needle in the tissues which were treated with the *Agrobacterium* strain. The plants obtained by culturing the tissues were tested for GUS activities. However, no plants exhibited GUS activity. The vicinity of the growth point is a very small tissue, so that it is not easy to pierce the needle into the very small tissue to infect *Agrobacterium*. The results of this experiment show that the transformation by infecting the vicinity of the growth point with *Agrobacterium* requires high skill in cutting out and piercing the growth point and the like.

TABLE 10

Introduction of Gene into Maize Shoot Apex Tissue

| Experiment | Number of Sample Tissues | Number of Tissues whose Apices shoot Extended | Number of Plants Obtained | Number of Plants in which GUS was Expressed |
|---|---|---|---|---|
| 1 | 24 | 9 | 2 | 0 |
| 2 | 16 | 8 | 6 | 0 |
| 3 | 17 | 13 | 5 | 0 |
| 4 | 14 | 1 | 0 | 0 |
| 5 | 45 | 14 | 7 | 0 |
| 6 | 32 | 14 | 8 | 0 |
| 7 | 30 | 7 | 1 | 0 |

Sample variety was P3732 in all experiments.

(10) Differences in Efficiencies of Gene Introduction Depending on Maize Varieties and on Strains In any of the varieties tested, expression of the GUS gene was observed at a high frequency. No differences were observed between the EHA101(pIG121Hm) and LBA4404 (pTOK232) (Table 10). The size of the stained area with respect to the entire callus was not less than 10% in many calli, so that the expression of the gene was observed in wide range of cells. The binary vectors pIG121Hm and pTOK232 used in this experiment do not express the GUS gene in *Agrobacterium* cells because the intron of castor bean is inserted in the promoter of the GUS gene. Therefore, the expression of the GUS gene observed in the maize calli indicates that gene introduction was carried out by the *Agrobacterium* strains with high frequency. After the culture with the *Agrobacterium* strains, from some of the sample calli, compact and knot-like calli grew. Since the grown cells exhibited expression of the GUS gene, it is thought that these cells are transformed cells. These compact and knot-like transformed calli can be regenerated into plants according to the method of Lupotto et al (Lupotto, E. and Lusardi, M. C. 1988; Maydica XXXIII:163–177).

TABLE 11

Introduction of Gene into Maize Shoot Apex Tissue

| Experiment | Number of Sample Tissue | Number of Tissues whose shoot Apices Extended | Number of Plants Obtained | Number of Plants in which GUS was Expressed |
|---|---|---|---|---|
| 1 | 24 | 9 | 2 | 0 |
| 2 | 16 | 8 | 6 | 0 |
| 3 | 17 | 13 | 5 | 0 |
| 4 | 14 | 1 | 0 | 0 |
| 5 | 45 | 14 | 7 | 0 |
| 6 | 32 | 14 | 8 | 0 |
| 7 | 30 | 7 | 1 | 0 |

Sample variety was P3732 in all experiments.

EXAMPLE 3

Transformation of Rice Cultured Tissue During Dedifferentiation (1) Variety of Rice TSUKINOHIKARI, which is a variety of japonica rice and which was also used in Example 1 was employed.

(2) Super Binary Vector pTOK233

Figure 2:
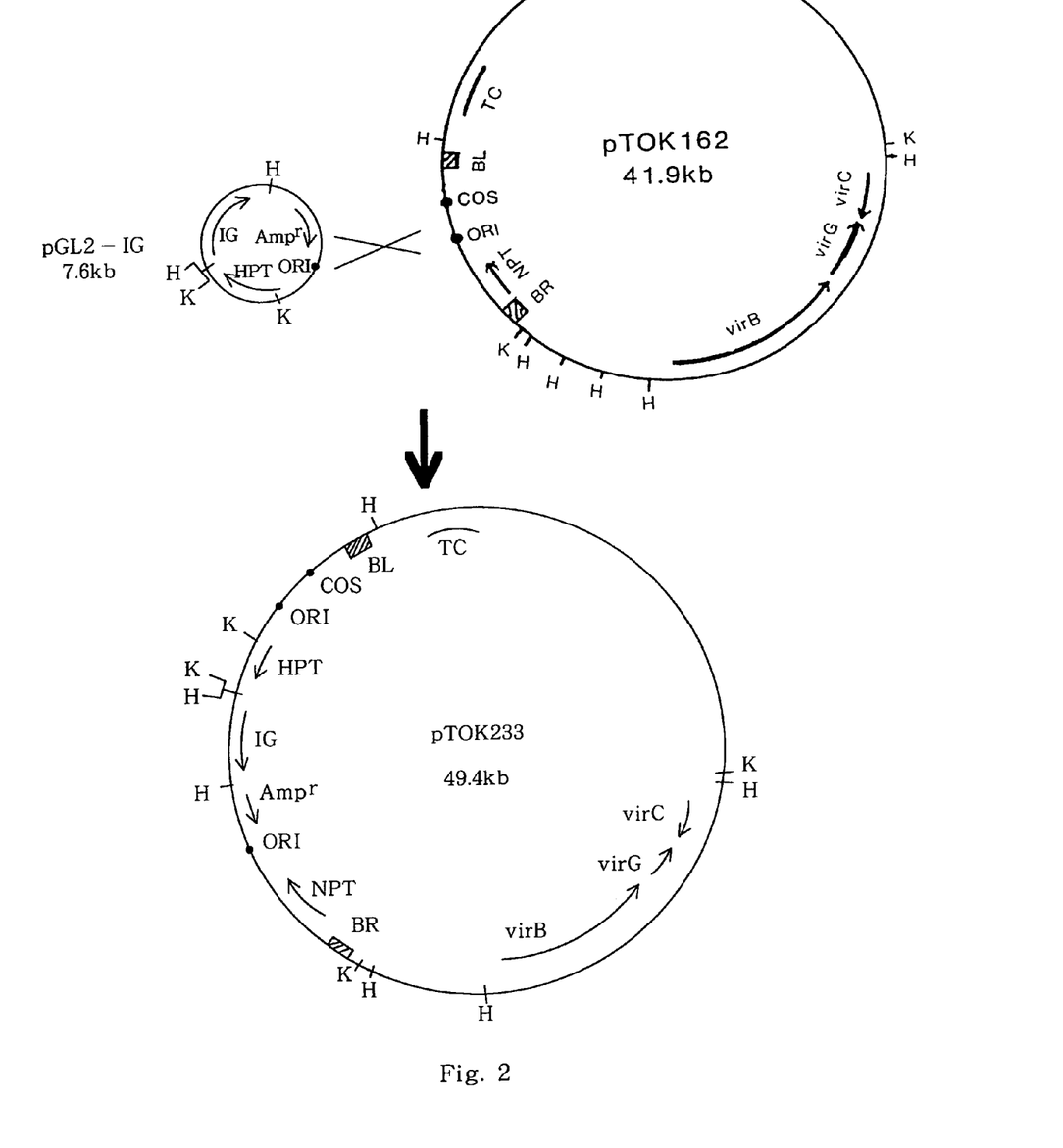
FIG. 2 shows the method for constructing a plasmid pTOK233 used in the examples of the present invention, which plasmid is similar to pTOK232.

A super binary vector pTOK233 was constructed by a process similar to the construction process of pTOK232, as shown in FIG. 2, from the above-described pGL2-IG and pTOK162.

(3) The Obtained Super Binary Vector pTOK233 or the Above-Described Binary Vector pIG121Hm was Introduced into Two Strains of *Agrobacterium tumefaciens* by the Same Method as Used in Example 1 to Obtain the Following Three *Agrobacterium tumefaciens* Strains.

LBA4404(pIG121Hm)
EHA101(pIG121Hm)
LBA4404(pTOK233)

All of these strains have an intron GUS and a hygromycin-resistance gene in the T-DNA region.

(4) Embryos of Mature Seeds

From mature rice seeds cultured on LS2.5 medium (LS basal medium supplemented with 2.5 mg/l of 2,4-dichlorophenoxyacetic acid) for 5 days (4 days post-germination), embryos (3–5 mm size) containing scutella were excised. The embryos were washed with sterilized water and immersed in a cell suspension of *Agrobacterium* as in Example 1. The embryos were then placed on 2N6 medium containing acetosyringone and cultured at 25° C. for 3 days in the dark. Expression of GUS gene was checked using X-gluc as in Example 1. The number of embryos which exhibited GUS expression on the scutella was counted.

(5) Embryos of Immature Seeds

Immature seeds at 10–14 days after flowering were sterilized and immature embryos (1.5–2.0 mm size) were excised. The embryos were sterilized by a conventional method and cultured on 2N6 medium for 2 days. The germinated buds were excised and immersed in *Agrobacterium* suspension as in Example 1. The embryos were then placed on 2N6 medium containing acetosyringone and cultured at 25° C. for 3 days in the dark.

(6) Selection of Resistant Cells and Regeneration

The embryos after the culture with *Agrobacterium* were placed on 2N6 medium containing 50 mg/l of hygromycin and 250 mg/l of cefotaxime and cultured at 25° C. for 3 weeks under illumination. The number of the tissues from which calli exhibiting uniform GUS expression were formed was counted. The selected calli were placed on N6–7 medium containing 100 mg/l of hygromycin and 250 mg/l of cefotaxime and cultured at 25° C. for 10 days under illumination. The selected calli were placed on N6S3 medium containing 50 mg/l of hygromycin and 250 mg/l of cefotaxime and cultured at 25° C. for 40 days under illumination. Using leaves of the obtained regenerated plants, expression of GUS gene was checked using X-gluc as in Example 1.

(7) Results

The results are shown in Tables 12–14 below.

TABLE 12

GUS Expression after Culturing with Agrobacterium (embryos derived from mature seeds)

| Sample Strain | Number of Sample Embryos | Number of GUS+ Embryos |
|---|---|---|
| EHA101 (pIG121Hm) | 50 | 8 |
|  | 61 | 11 |
| LBA4404 (pTOK233) | 53 | 16 |
|  | 60 | 32 |

TABLE 13

Results of Transformation (embryos derived from mature seeds)

| | | Number of Lines | | |
|---|---|---|---|---|
| Sample Strain | Number of Sample Tissues | Hygromycin-resistant and GUS+ Calli | Calli Yielded Regenerated Plants | GUS+ Regenerated Plants |
| EHA101 (pIG121Hm) | 43 | 0 | 0 | 0 |
|  | 78 | 2 | 0 | 0 |
| LBA4404 (pTOK233) | 50 | 1 | 1 | 1 |
|  | 80 | 8 | 5 | 5 |

TABLE 14

Results of Transformation (embryos derived from immature seeds)

| | | Number of Lines | | |
|---|---|---|---|---|
| Sample Strain | Number of Sample Tissues | Hygromycin-resistant and GUS+ Calli | Calli Yielded Regenerated Plants | GUS+ Regenerated Plants |
| LBA4404 (pIG121Hm) | 65 | 10 | 4 | 3 |
| EHA101 (pIG121Hm) | 67 | 15 | 6 | 6 |
|  | 41 | 8 | 3 | 3 |
| LBA4404 (pTOK233) | 65 | 41 | 28 | 25 |
|  | 40 | 28 | 17 | 13 |

As can be seen from Table 12, with the embryos derived from mature seeds, the number of embryos which showed GUS expression was much larger in the group treated with LBAA4404(pTOK233). As can be seen from Table 13, hygromycin-resistant calli were scarcely obtained in the group treated with EHA101(pIG121Hm) and no regenerated plants were obtained in this group. In contrast, in the group treated with LBA4404(pTOK233), regenerated plants were obtained even though the frequency was low. Most of the regenerated plants expressed GUS and so they are thought to be transformants.

As can be seen from Table 14, with the immature embryos, transformants were obtained in all groups irrespective of the strain used for transformation. However, the transformation efficiency was prominently high when LBA4404(pTOK233) was used.

Thus, the embryo tissues cultured in a dedifferentiation-inducing medium for several days were able to be transformed via *Agrobacterium*. For such transformation, a super binary vector such as pTOK233 contained in the strain LBA4404(pTOK233) gives prominently high transformation efficiency and so is very useful for this purpose.

The invention claimed is:

1. A method for transforming a monocot plant comprising:
   i) culturing an explant of said monocot plant, or a tissue isolated from said explant, for one to six days in a medium comprising at least one auxin to obtain a cultured tissue;
   ii) co-culturing the cultured tissue from step i) with an *Agrobacterium* bacterium comprising a polynucleotide of interest;
   iii) selecting cultured tissue into which the polynucleotide of interest has been introduced; and
   iv) culturing the selected tissue on a regeneration medium to obtain a transformed monocot plant.

2. The method of claim 1, in which the explant is from a seed or an embryo of said monocot plant.

3. The method of claim 2 further comprising a step
   ia) of isolating a scutellum tissue from the seed or embryo of the monocot plant as the cultured tissue.

4. The method of claim 3 in which the scutellum tissue forms a callus and the callus tissue is used in the co-culturing step ii).

5. The method of claim 4 in which the scutellum callus is made into a suspension culture for the co-culturing step ii).

6. The method of claim 2, wherein an immature embryo tissue is cultured in step i).

7. The method of claim 1, in which the *Agrobacterium* bacterium comprises a vector comprising at least one virulence gene of a Ti plasmid, a left T-DNA border, a right T-DNA border and the polynucleotide of interest located between the left T-DNA border and the right T-DNA border.

8. The method of claim 7, wherein the at least one virulence gene is at least the VirB and VirG genes.

9. The method of claim 7, in which the vector is a super binary vector that comprises at least one virulence gene from the Ti plasmid pTiBo542 of *Agrobacterium tumefaciens* A281.

10. The method of any one of claims 1–9, wherein the plant is one from the family Gramineae.

11. The method of any one of claims 1–9 wherein the plant is a rice plant.

12. The method of any one of claims 1–6 wherein the *Agrobacterium* bacterium is *Agrobacterium tumefaciens*.

13. The method of any one of claims 1–6, wherein the bacteria are present in an amount of $10^6$ to $10^{11}$ cells/ml.

14. The method of any one of claims 1–6, wherein the contacting step ii) is performed in a liquid medium for 3 to 10 minutes, and then maintaining the contacted cultured tissue and *Agrobacterium* cells on a solid medium.

15. The method of claim 7, wherein the at least one virulence gene is at least one virulence gene from the plasmid pTOK162.

16. A method for transforming a tissue of a monocot plant comprising:
   i) culturing an explant of an immature tissue of a monocot plant for one to six days on a medium comprising at least one auxin and that induces dedifferentiation of the cells of the explanted tissue to obtain a dedifferentiating or dedifferentiated cultured immature tissue;
   ii) contacting the dedifferentiating or dedifferentiated cultured immature tissue with cells of *Agrobacterium* bacteria that comprise a vector comprising at least one virulence gene of a Ti plasmid, a left T-DNA border, a right T-DNA border and a polynucleotide of interest located between the left T-DNA border and the right T-DNA border;
thereby obtaining a transformed plant tissue.

17. The method of claim 16, wherein the immature tissue is an immature embryo tissue.

18. The method of claim 16 or 17, wherein the plant is one from the family Gramineae.

19. The method of 18 wherein the plant is a rice plant.

20. A method for obtaining a transformed monocot plant comprising
   i) culturing an explant of an immature tissue of a monocot plant for one to six days on a medium comprising at least one auxin and that induces dedifferentiation of the cells of the explanted tissue to obtain a dedifferentiating or dedifferentiated cultured immature tissue;
   ii) contacting the dedifferentiating or dedifferentiated cultured immature tissue with cells of *Agrobacterium* bacteria that comprise a vector comprising at least one virulence gene of a Ti plasmid, a left T-DNA border, a right T-DNA border and a polynucleotide of interest located between the left T-DNA border and the right T-DNA border; thereby obtaining a transformed plant tissue; and
   iii) culturing the transformed plant tissue on at least one regeneration medium, thereby obtaining a transformed monocot plant.

* * * * *